United States Patent

Fox et al.

Patent Number: 5,273,524
Date of Patent: Dec. 28, 1993

[54] ELECTROSURGICAL DEVICE

[75] Inventors: William D. Fox, New Richmond; Richard F. Schwemberger, Cincinnati; Edward J. Biehle, IV, Westchester; Harry C. Parkhurst, Cincinnati, all of Ohio

[73] Assignee: Ethicon, Inc., Somerville, N.J.

[21] Appl. No.: 773,401

[22] Filed: Oct. 9, 1991

[51] Int. Cl.$^5$ .............................. A61N 1/30
[52] U.S. Cl. .................... 604/21; 604/22; 606/37; 606/45
[58] Field of Search .............. 604/20, 21, 22, 27; 128/783, 800; 606/32, 37, 39, 40–42, 45, 46, 49

[56] References Cited

U.S. PATENT DOCUMENTS

| | | | |
|---|---|---|---|
| 3,828,780 | 8/1974 | Morrison, Jr. | 604/20 |
| 3,974,833 | 8/1976 | Durden, III | 604/20 |
| 4,034,761 | 7/1977 | Prater et al. | 128/303.14 |
| 4,307,720 | 12/1981 | Weber, Jr. | 604/22 |
| 4,655,215 | 4/1987 | Pike | 128/303.14 |
| 4,674,499 | 6/1987 | Pao | 604/20 |
| 4,688,569 | 8/1987 | Rabinowitz | 128/303.14 |
| 4,719,914 | 1/1988 | Johnson | 606/45 |
| 4,838,246 | 6/1989 | Hahn | 128/6 |
| 4,867,141 | 9/1989 | Nakada et al. | 128/24 AA |
| 4,872,454 | 10/1989 | DeOliveira et al. | 606/45 |
| 4,924,851 | 5/1990 | Ognier et al. | 128/4 |
| 4,931,047 | 6/1990 | Broadwin et al. | 606/45 |
| 5,011,483 | 4/1991 | Sleister | 606/37 |
| 5,015,227 | 5/1991 | Broadwin et al. | 606/45 |
| 5,035,695 | 7/1991 | Weber, Jr. et al. | 606/42 |

*Primary Examiner*—C. Fred Rosenbaum
*Assistant Examiner*—Michael Rafa
*Attorney, Agent, or Firm*—Paul A. Coletti

[57] ABSTRACT

An electrosurgical device for laparoscopic use in tissue dissection and coagulation. The device includes a barrel member having a dissection tip at the distal end thereof that is connected to a source of electrical energy. An insulating sheath member surrounds the barrel member. The sheath member is movable between a first position wherein the distal end thereof extends distally beyond the dissection tip and a second position wherein the dissection tip extends distally beyond the distal end portion of the sheath member. The device includes means to flush and vacuum the surgical site. The device also includes pressure relief means to limit the internal pressure within the device.

18 Claims, 2 Drawing Sheets

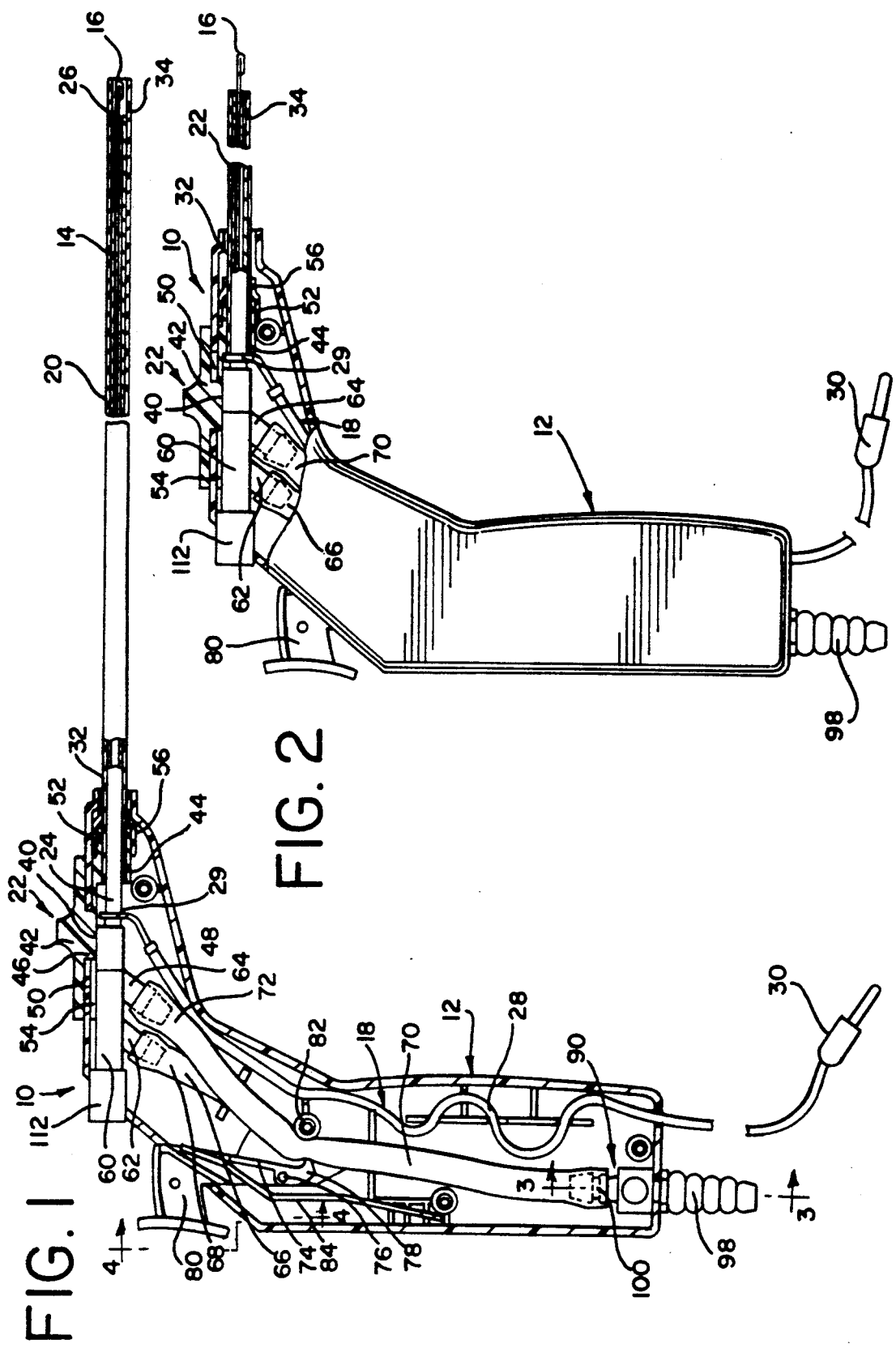

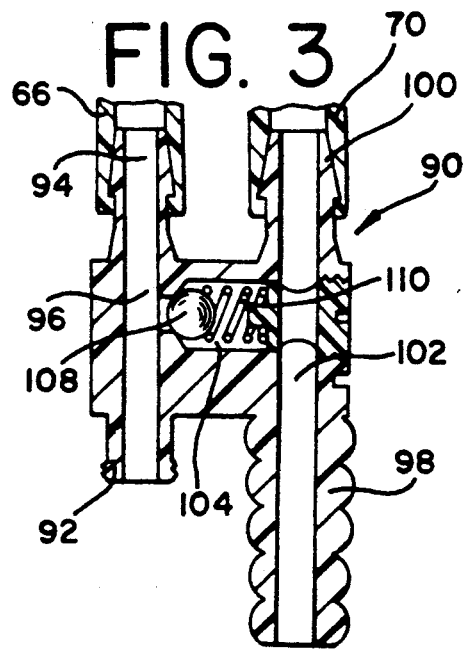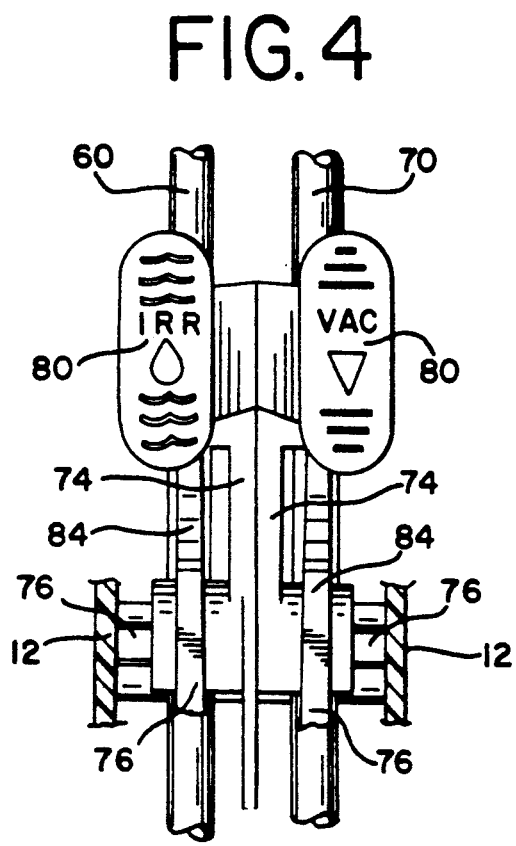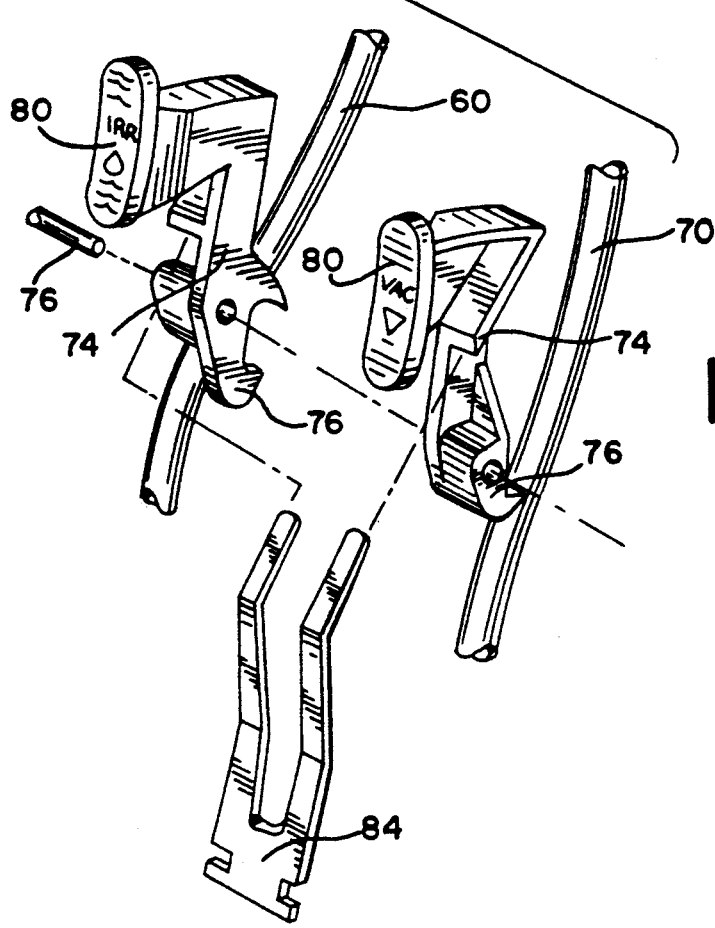

ELECTROSURGICAL DEVICE

FIELD OF THE INVENTION

This invention generally relates to an electrosurgical or electrocautery device for use in tissue dissection and coagulation. More particularly, the invention relates to a disposable electrosurgical device that is adapted for use laparoscopically through a trocar tube.

BACKGROUND OF THE INVENTION

Surgery using laparoscopic procedures is gaining popularity among surgeons due to patient demand for less invasive surgery. Electrosurgical or electrocautery devices are well known for use in cutting and coagulating tissue. A common use of these devices laparoscopically is in a procedure called cholecystectomy, or gallbladder removal. There have been some reported instances of injuries caused by such use of known electrosurgical devices. One known potential injury is organ burn, which may occur with inadvertent direct contact of the tip of the instrument with the organ or when an electrical charge from the device jumps or sparks to the organ.

Electrosurgical devices have heretofore included an insulated barrel that terminates in an electrically conductive dissection tip extending outward from the distal end thereof. The dissection tip is in electrical communication with a monopolar electrosurgical generator (ESU). These ESU's typically generate two types of radio frequency electrosurgical waveforms; namely, a "Cut" and a "Coag" waveform. It is known to provide electrosurgical devices with means to selectively irrigate or flush the surgical site with liquids and vacuum means to selectively remove excess body fluids and irrigation liquids from the surgical site.

In order to protect the dissection tip it is known to provide a tubular shield member that slips over the distal end of the barrel in surrounding relationship with respect to the dissection tip. Prior to use, it is necessary to remove the tubular shield member. Upon removal of the shield member and insertion of the barrel through a trocar tube during a laparoscopic procedure, the surgeon no longer has the ability to cover or shield the dissecting tip. As alluded to above, an unshielded dissecting tip may cause damage to body organs. Also, insertion and extraction of an unshielded tip may cause damage to the seal members associated with the trocar assembly.

It has heretofore been proposed to protect the dissection tip by providing a remote means to retract the dissection tip. This device includes structural elements located in the barrel that preclude use of the barrel to direct instruments therethrough.

There is a need for an electrosurgical device that includes a retractable electrode sheath that may be remotely and selectively controlled by the surgeon to protect the dissection tip and the trocar assembly seal during insertion and retraction and to protect body organs during surgery. There is further a need for an electrosurgical device that may be operated with one hand and that may accept instruments therethrough. There also is a need for an electrosurgical device that is safe and reliable in operation and economical to manufacture.

SUMMARY OF THE INVENTION

In accordance with the principles of the present invention, an electrosurgical device is provided that includes a handle member having an elongated barrel member that may be directed through an appropriately sized trocar tube. The barrel member has a proximal end portion rigidly secured to the handle member and distal end portion. A suitable electrode member or dissection tip is secured to and extends outwardly from the distal end portion of the barrel member. The electrode member is connected to a source of electrical energy through an electrical cord and plug assembly.

An insulating sheath member, having a proximal end portion and a distal end portion, is positioned in surrounding relationship with the barrel member. The proximal end portion of the sheath member extends into the handle member. The sheath member is movable between a first position wherein the distal end portion thereof extends distally beyond a distal end portion of the electrode member and a second position wherein a distal end portion of the electrode member extends distally beyond the distal end portion of the sheath member. A control means permits selective movement of the sheath member between its first and second positions.

The control means may include a slide member that is secured to the proximal end portion of the sheath member. The slide member is attached to the handle member so as to permit movement thereof between a first position wherein the sheath member is in its first position and a second position wherein the sheath member is in its second position.

The handle member may be provided with an access port that communicates with the proximal end portion of the barrel member for receipt of an instrument therethrough.

The device is preferably provided with means to selectively irrigate or flush the surgical site with liquids and vacuum means to selectively remove excess body fluids and irrigation liquids from the surgical site. In accordance with a preferred embodiment, a manifold member is located in the handle member in communication with the proximal end portion of the barrel member. An irrigation tube is positioned in the handle member having a first end portion in communication with the manifold member and a second end portion adapted to be connected to an irrigation unit. A vacuum tube is positioned in the handle member having a first end portion in communication with the manifold member and a second end portion adapted to be connected to a vacuum source. The irrigation tube and the vacuum are provided with separate flow control means for selectively permitting and precluding fluid flow through the tubes.

Each flow control means includes a pivotal lever member selectively movable between a first position permitting flow through the corresponding tube and a second position pinching the corresponding tube so as to preclude flow therethrough. The pivotal member is spring biased into its second position. A corresponding button member extends outwardly through the handle member for controlling the movement of each of the lever members between their first and second positions.

A pressure relief means is preferably provided to limit the internal pressure within the device to about 50 psig. A connector assembly is located in the handle member. The connector assembly includes an irrigation inlet port adapted to be connected to an irrigation unit and an irrigation outlet port connected to the second end portion of the irrigation tube. The irrigation tube is in fluid communication with the irrigation inlet port through an irrigation flow channel extending therebetween. The connector assembly also includes a vacuum inlet port adapted to be connected to a vacuum source and a vacuum outlet port connected to the second end portion of the vacuum tube in fluid communication with the vacuum inlet port through a vacuum flow channel extending therebetween. A shunt channel extends between the irrigation and vacuum flow channels. A pressure vent valve member is located in the shunt channel to vent excess pressure in the irrigation flow channel through the shunt channel into the vacuum flow channel.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference numerals indicate the same or similar components, wherein:

FIG. 1 is a cross-sectional view of an electrosurgical device constructed in accordance with the present invention showing the sheath member in its first position;

FIG. 2 is an elevational view, partially broken away, of the electrosurgical device shown in FIG. 1 showing the sheath member in its second position;

FIG. 3 is a cross-sectional view taken along line 3—3 in FIG. 1 showing a pressure vent connector assembly constructed in accordance with the invention;

FIG. 4 is a cross-sectional view taken along line 4—4 in FIG. 1 showing the flow control means in accordance with the invention; and FIG. 5 is an exploded perspective view of the flow control means as shown in FIG. 4.

DETAILED DESCRIPTION OF THE PREFERRED EMBODIMENTS

Referring to FIG. 1, there is shown an electrosurgical or electrocautery device 10 for use in tissue dissection, coagulation, irrigation, and fluid evacuation. Device 10 is a hand-held, disposable surgical instrument intended to be used to perform various surgical procedures, such as cholecystectomies (gall bladder removal) and appendectomies (appendix removal). The device is used laparoscopically through a 5 mm (or similarly sized) trocar tube or cannula to perform minimally invasive surgical techniques that replace prior open surgery methods.

Electrosurgical device 10 includes a handle member 12, an elongated barrel member 14, an electrode member 16, a means 18 for connecting the electrode member 16 to a source of electrical energy, an insulating sheath member 20, and a control means 22 for controlling the movement of the sheath member. In accordance with a preferred embodiment, handle member 12 is a pistol-style grip that may be held in one hand in two alternative attitudes.

Barrel member 14 is a hollow cylindrical member made from a conductive metallic material, such as stainless steel. Barrel member 14 has a proximal end portion 24 that extends into handle member 12 and is rigidly attached thereto. Distal end portion 26 of barrel member 14 has a suitable electrode member or dissection tip 16 rigidly secured thereto. Electrode member 16 may take one of many known forms, such as a hook, spatula, ballpoint, or the like. Electrical energy is supplied to the electrode member 16 through a means 18 which may include an electrical cord 28 extending through the butt end of handle member 12. Cord 28 at one end is attached to the proximal end 24 of barrel member 14 through a connecting ring 29 and at the other end is connected to a "banana" jack 30 which plugs into a mating jack (not shown) in one of several possible monopolar electrosurgical generators (ESU's) that are well known in the art. These ESU's typically generate two types of radio frequency electrosurgical waveforms; namely, "Cut" and "Coag." The selection of the particular mode of operation may be regulated by a foot control pedal associated with the ESU.

In accordance with a unique feature of the invention, an insulating sheath member 20 is provided in surrounding relationship to barrel member 14. Sheath member 20 is preferably a hollow cylindrical member made from a suitable material, such as Teflon FEP. Sheath member 20 has a proximal end portion 32 that is received in handle member 12 so as to permit reciprocal movement thereof in a manner that will be further described hereinbelow. Sheath member 20 has a distal end portion 34. Sheath member 20 is movable between a first position wherein distal end portion 34 extends distally beyond the distal end of electrode member 16, as seen in FIG. 1, and a second position wherein the distal end of electrode member 16 extends distally beyond the distal end portion 34 of sheath member 20, as seen in FIG. 2.

As one can appreciate, when sheath member 20 is in its first position, the tip of electrode member 16 is shielded to protect against the electrode member 16 inadvertently contacting body organs when not in use and to protect the seal associated with the trocar assembly as the electrode member 16 is inserted or withdrawn therefrom. When sheath member 20 is in its second position, the electrode or dissecting tip 16 is exposed for use in a well known manner.

Control means 22 selectively controls the movement of the sheath member between its first and second positions. Control means 22 includes a slide member 40 that is attached to the proximal end portion 32 of the sheath member and is movable therewith. Slide member 40 includes a thumb activated activator portion 42 that is located exterior of the top of handle member 12 and a connector portion 44 that is received around the proximal end portion 34 of the sheath member within handle member 12. A guide portion 46 extends between activator portion 42 and connector portion 44. Guide portion 46 includes a slide section 48 that extends through an elongated slot or opening 50 formed in handle member 12. Guide portion 46 includes a forward leaf section 52 and a rearward leaf section 54 that are spaced from activator portion 42 and slidably receive corresponding portions of handle member 12 that are forward and rearward of slot 50 therebetween. Connector portion 42 extends from leaf section 52. Forward and rearward movement of activator portion 42 causes slide section 46 to move between the forward and rearward ends of slot 50 and thereby move sheath member 20 between its first and second positions. Connector portion 44 is secured to proximal end portion 34 by a plastic, such as polyethylene, shrink tube 56.

The proximal end portion 24 of barrel member 14 extends into and is in fluid communication with a tubular manifold member 60 positioned in handle member 12. Manifold member 60 is in axial alignment with barrel member 14 and is formed with an irrigation port or fitting 62 and a vacuum port or fitting 64. An irrigation tube 66 is positioned in handle member 12 having a first end portion 68 connected to port 62 and a second end portion adopted to be connected to an irrigation unit in a manner as further described hereinbelow. A vacuum tube 70 is positioned in handle member 12 having a first end portion 72 connected to port 64 and a second end portion adapted to be connected to a vacuum source as described hereinbelow.

Referring to FIGS. 1, 4 and 5, a unique flow control means is provided to selectively permit and preclude flow through each of the tubes 66 and 70. The flow control means for each of the tubes are substantially identical and are located in a side by side relationship. Accordingly, only the flow control means associated with vacuum tube 70 shall be described in detail herein. The vacuum flow control means includes a pivotal level member 74 that is pivotally mounted within handle member 12 about pivot pin 76. Lever member 74 includes a tube pinching portion 78 and a thumb-actuated button portion 80. Pivotal movement of lever member 74 causes portion 78 to move between a first position permitting flow or the creation of a vacuum through the tube and a second position pinching the tube precluding flow or the creation of a vacuum through the tube. As shown in FIG. 1, when lever member 74 is in its second position, tube 70 is pinched between portion 78 and a post member 82 located in the handle member. Button portion 80 extends outwardly through an opening in the handle member for controlling the pivotal movement of lever member 74 between its first and second positions. A leaf spring member 84 biases lever member 74 into its second position.

In accordance with a unique feature of the invention, a pressure vent means is provided in communication with irrigation tube 66 for venting excess pressure therein. Referring to FIG. 3, a connector assembly 90 is positioned in the handle member 12. Assembly 90 includes an irrigation inlet port or female Luer lock fitting 92 adapted to be connected to an irrigation unit and an irrigation outlet port 94 connected to the second end portion of irrigation tube 66. Tube 66 is in fluid communication with inlet port 92 through an irrigation flow channel 96 extending therebetween. The irrigation unit may induce a constant or variable pressure medical irrigation pump, peristaltic pump, IV bag, or rubber squeeze bulb. Assembly 90 further includes a vacuum inlet port or male fitting 98 adapted to be connected to an electric vacuum pump and a vacuum outlet port 100 connected to the second end portion of the vacuum tube 70. Tube 70 is in fluid communication with inlet port 98 through a vacuum flow channel 102 extending therebetween. A shunt channel 104 extends between channels 96 and 102.

A pressure vent means 106 is positioned in shunt channel 104 to vent excess pressure in irrigation flow channel 96 and irrigation tube 66 through the shunt channel 104, vacuum flow channel 102 and vacuum tube 70. Pressure vent means 106 preferably includes a check ball valve member 108 that is biased into a position precluding flow through shunt channel 104 by a spring member 110. Spring member 110 is preferably selected to preclude the internal pressure in the irrigation tube 66 from exceeding about 50 psig. Pressure vent means 106 protects the device 10 and the irrigation pumps.

An access port 112 may be provided in axial alignment with manifold member 60 and barrel member 14 for insertion of implements through access port 112, manifold member 60 and barrel member 14. Access port 112 is preferably made of silicone rubber.

The unique features of the electrosurgical device 10 in accordance with the invention will become apparent from the following description of the basic operation thereof. A patient grounding pad (return electrode) is firmly affixed to the patient in an area that is electrically near the operation site in a well known manner. The grounding pad is the return path for monopolar electrical current to return to the ESU unit. The single patient use disposable device 10 is removed from its sterile package. A vacuum line (not shown) is pushed onto the inlet port 98 and an irrigation supply line (not shown) is connected to the Luer lock fitting 92. The universal electrosurgical banana jack 30 plugs into a universal adapter or directly into the ESU unit. The vacuum, irrigation, and the ESU units are turned on and the device is ready for use.

In many laparoscopic operations, the abdomen of the patient is first inflated using a hollow air needle. Two or more trocar tubes are typically then pierced through the abdominal wall to provide paths for introducing an endoscope and other laparoscopic instruments, such as electrosurgical device 10. An endoscope is necessary for viewing the procedure on a CRT monitor.

At such time as the use of electrosurgical device 10 is required, the barrel member 14 with the sheath member 20 in its first position (as shown in FIG. 1) is directed through a 5 mm trocar tube into the operation site. The surgeon may conveniently expose the dissection tip 16 by moving control means 22 into its second position causing sheath 20 to move into its second position (as shown in FIG. 2). The surgeon may energize the dissection tip to the appropriate power level ("Cut" or "Coag") using the ESU foot pedal.

After a period of dissection, the operation site can be rinsed by depressing the irrigation button 80 on the handle, causing the irrigation lever member 74 to move into its first position against the bias of spring member 84. Rinsing stops when the irrigation button 80 is released and the irrigation lever member 74 returns to its second position. After rinsing, vacuum button 80 may be depressed to move vacuum lever member 74 into its first position against the bias of spring member 84 to vacuum the fluids from the site. Although not shown, buttons 80 may be provided with a lock to selectively retain the buttons in their first positions.

The sheath member 20 may be moved into its first position in covering relationship to dissecting tip 16 at any time during the procedure by moving control 22 into its first position which in turn causes sheath member 20 to move into its first position. This function is particularly useful in protecting delicate organs during the vacuum function, and during introduction and withdrawal of barrel member 14 through the trocar tube.

When the surgical repair is completed, the barrel member 14 is withdrawn from the trocar tube and the device 10 is unhooked from the pumps and ESU unit, and is discarded.

From the foregoing, it will be observed that numerous modifications and corrections can be effected without departing from the true spirit and scope of the novel concepts of the present invention. It will be understood that no limitation with respect to the specific embodiment illustrated herein is intended or should be inferred.

It is, of course, intended to cover by the appended claims all such modifications as fall within the scope of the claims.

What is claimed is:

1. An electrosurgical device, comprising:
a handle member;
an elongated barrel member having a proximal end portion and a distal end portion, said proximal end portion being rigidly secured to said handle member;
an electrode member extending outwardly from the distal end portion of said barrel member;
means for connecting said electrode member to a source of electrical energy;
an insulating sheath member surrounding said barrel member, said sheath member having a proximal end portion extending into said handle member and a distal end portion, said sheath member being movable with respect to said barrel member between a first position wherein said distal end portion of said sheath member extends distally beyond the distal end of said electrode member and a second position wherein the distal end portion of said electrode member extends distally beyond said distal end portion of said sheath member;
control means for selectively controlling the movement of said sheath member between its first and second positions, wherein said control means includes a slide member being attached to said handle member so as to permit movement thereof between a first position wherein said sheath member is in its first position and a second position wherein said sheath member is in its second position; and wherein said slide member includes a activator portion that is positioned exterior of said handle member and a connector portion that is positioned inside said handle member and is secured to said proximal end portion of said sheath member, and a guide portion that extends between said activator portion and said connector portion, said guide portion including a slide section that extends through an elongated slot formed in said handle member.

2. The electrosurgical device as defined in claim 1 wherein said guide portion further includes a forward leaf section and a rearward leaf section, said forward and rearward leaf sections being spaced from said activator portion for sliding receipt of portions of said handle member forward and rearward of said elongated slot therebetween.

3. The electrosurgical device as defined in claim 1 wherein said handle member includes an access port that communicates with the proximal end portion of said barrel member.

4. The electrosurgical device as defined in claim 1 further including:
a manifold member positioned in said handle member, said manifold member being in communication with the proximal end portion of said barrel member;
an irrigation tube positioned in said handle member, said irrigation tube having a first end portion in communication with said manifold member and a second end portion adapted to be connected to an irrigation unit; and
a vacuum tube positioned in said handle member, said vacuum tube having a first end portion in communication with said manifold member and a second end portion adapted to be connected to a vacuum source.

5. The electrosurgical device as defined in claim 4 further including irrigation flow control means for selectively permitting and precluding the flow of irrigation fluid through said irrigation tube.

6. The electrosurgical device as defined in claim 5 wherein said irrigation flow control means includes a pivotal lever member selectively movable between a first position permitting flow of irrigating fluid through said irrigation tube and a second position pinching said irrigation tube so as to preclude the flow of irrigating fluid through said irrigation tube.

7. The electrosurgical device as defined in claim 6 wherein said pivotal lever member is spring biased into its second position.

8. The electrosurgical device as defined in claim 7 wherein said irrigation flow control means includes a button member that extends outwardly through an opening in said handle member for controlling the movement of said lever member between its first and second positions.

9. The electrosurgical device as defined in claim 4 further including vacuum flow control means for selectively permitting and precluding the creation of a vacuum through said vacuum tube.

10. The electrosurgical device as defined in claim 9 wherein said vacuum flow control means includes a pivotal lever member selectively movable between a first position creating a vacuum through said vacuum tube and a second position pinching said vacuum tube so as to preclude the creation of a vacuum through said vacuum tube.

11. The electrosurgical device as defined in claim 10 wherein said vacuum control means is spring biased into its second position.

12. The electrosurgical device as defined in claim 11 wherein said vacuum control means includes a button member that extends outwardly through an opening in said handle member for controlling the movement of said lever member between its first and second positions.

13. The electrosurgical device as defined in claim 4 further including a connector assembly, said connector assembly having an irrigation inlet port adapted to be connected to an irrigation unit and an irrigation outlet port connected to the second end portion of said irrigation tube in fluid communication with said irrigation inlet port through an irrigation flow channel extending therebetween, said connector assembly having a vacuum inlet port adapted to be connected to a vacuum source and a vacuum outlet port connected to the second end portion of said vacuum tube in fluid communication with said vacuum inlet port through a vacuum flow channel extending therebetween.

14. An electrosurgical device, comprising:
a handle member;
an elongated barrel member having a proximal end portion and a distal end portion, said proximal end portion being rigidly secured to said handle member;
an electrode member extending outwardly from the distal end portion of said barrel member;
means for connecting said electrode member to a source of electrical energy;
an insulating sheath member surrounding said barrel member, said sheath member having a proximal end portion extending into said handle member and a distal end portion, said sheath member being movable with respect to said barrel member between a first position wherein said distal end portion of said sheath member extends distally beyond the distal end of said electrode member and a second position wherein the distal end portion of said electrode member extends distally beyond said distal end portion of said sheath member;

control means for selectively controlling the movement of said sheath member between its first and second positions;

a manifold member positioned in said handle member, said manifold member being in communication with the proximal end portion of said barrel member;

an irrigation tube positioned in said handle member, said irrigation tube having a first end portion in communication with said manifold member and a second end portion adapted to be connected to an irrigation unit;

a vacuum tube positioned in said handle member, said vacuum tube having a first end portion in communication with said manifold member and a second end portion adapted to be connected to a vacuum source;

a connector assembly, said connector assembly having an irrigation inlet port adapted to be connected to an irrigation unit and an irrigation outlet port connected to the second end portion of said irrigation tube in fluid communication with said irrigation inlet port through an irrigation flow channel extending therebetween, said connector assembly having a vacuum inlet port adapted to be connected to a vacuum source and a vacuum outlet port connected to the second end portion of said vacuum tube in fluid communication with said vacuum inlet port through a vacuum flow channel extending therebetween.

wherein said connector assembly includes a shunt channel extending between said irrigation flow channel and said vacuum flow channel, said shunt channel having a pressure vent valve member associated therewith to vent excess pressure in said irrigation flow channel through said shunt channel into said vacuum flow channel.

15. The electrosurgical device as defined in claim 14 wherein said pressure vent valve member is a spring biased check ball valve located in said shunt channel.

16. The electrosurgical device as defined in claim 14 wherein said pressure vent valve member limits the internal pressure in said irrigation flow channel to about 50 psig.

17. An electrosurgical device, comprising:

a handle member;

an elongated barrel member having a proximal end portion and a distal end portion;

an electrode member extending outwardly from the distal end portion of said barrel member;

means for connecting said electrode member to a source of electrical energy;

a manifold member positioned in said handle member in communication with the proximal end portion of said barrel member;

an irrigation tube positioned in said handle member, said irrigation tube having a first end portion in communication with said manifold member and a second end portion adapted to be connected to an irrigation unit;

a vacuum tube positioned in said handle member, said vacuum tube having a first end portion in communication with said manifold member and a second end portion adapted to be connected to a vacuum source;

pressure vent means in communication with said irrigation tube for venting excess pressure therefrom, wherein said pressure vent means precludes the internal pressure in said irrigation tube from exceeding about 50 psig; and a connector assembly positioned in said handle member, said connector assembly having an irrigation inlet port adapted to be connected to an irrigation unit and an irrigation outlet port connected to the second end portion of said irrigation tube in fluid communication with said irrigation inlet port through an irrigation flow channel extending therebetween, said connector assembly having a vacuum inlet port adapted to be connected to a vacuum source and a vacuum outlet port connected to the second end portion of said vacuum tube in fluid communication with said vacuum inlet port through a vacuum flow channel extending therebetween, said connector assembly having a shunt channel extending between said irrigation flow channel and said vacuum flow channel, said pressure vent means being positioned in said shunt channel to vent excess pressure in said irrigation flow channel through said shunt channel into said vacuum flow channel.

18. The electrosurgical device as defined in claim 17 wherein said pressure vent means is a spring biased check ball valve.

* * * * *